United States Patent [19]
Geddes et al.

[11] Patent Number: 5,916,239
[45] Date of Patent: Jun. 29, 1999

[54] METHOD AND APPARATUS USING VAGAL STIMULATION FOR CONTROL OF VENTRICULAR RATE DURING ATRIAL FIBRILLATION

[75] Inventors: Leslie A. Geddes, West Lafayette, Ind.; Tarek Elabbady, Redmond, Wash.; William E. Schoenlein, Lafayette, Ind.; Matthew Waninger, Frankfort, Ind.; Joe D. Bourland, West Lafayette, Ind.

[73] Assignee: Purdue Research Foundation, West Lafayette, Ind.

[21] Appl. No.: 08/976,854

[22] Filed: Nov. 24, 1997

Related U.S. Application Data

[63] Continuation-in-part of application No. 08/624,109, Mar. 29, 1996, Pat. No. 5,690,681.

[51] Int. Cl.$^6$ .................................................. A61N 1/362
[52] U.S. Cl. .............................................................. 607/14
[58] Field of Search .................................. 607/2, 4, 5, 9, 607/14, 44; 600/16, 17

[56] References Cited

U.S. PATENT DOCUMENTS

| | | |
|---|---|---|
| 3,650,277 | 3/1972 | Sjostrand et al. . |
| 3,796,221 | 3/1974 | Hagfors . |
| 3,850,161 | 11/1974 | Liss . |
| 3,918,461 | 11/1975 | Cooper . |
| 4,280,502 | 7/1981 | Baker et al. . |
| 4,573,481 | 3/1986 | Bullara . |
| 4,867,164 | 9/1989 | Zabara . |
| 4,890,617 | 1/1990 | Markowitz et al. . |
| 4,998,974 | 3/1991 | Aker . |
| 5,086,772 | 2/1992 | Larnard et al. . |
| 5,107,850 | 4/1992 | Olive . |
| 5,144,947 | 9/1992 | Wilson . |
| 5,154,172 | 10/1992 | Terry et al. . |
| 5,193,550 | 3/1993 | Duffin . |
| 5,199,428 | 4/1993 | Obel et al. . |
| 5,203,326 | 4/1993 | Collins . |
| 5,215,089 | 6/1993 | Baker . |
| 5,222,494 | 6/1993 | Baker . |
| 5,243,980 | 9/1993 | Mehiz . |
| 5,330,507 | 7/1994 | Schwartz . |
| 5,335,657 | 8/1994 | Terry et al. . |
| 5,480,413 | 1/1996 | Greenhut et al. . |
| 5,522,852 | 6/1996 | White et al. . |
| 5,700,282 | 12/1997 | Zabara ....................................... 607/9 |

FOREIGN PATENT DOCUMENTS

| | | |
|---|---|---|
| 0 688 577A1 | 12/1995 | European Pat. Off. . |
| WO 93/21824 | 11/1993 | WIPO . |

OTHER PUBLICATIONS

Jaeho Kim, Joe Bocek, Harley White, Bill Crone, Cliff Alferness, John Adams, "An Atrial Fibrillation Detection Algorithm for an Implantable Atrial Defibrillator," *Computers in Cardiology 1995*, Sept. 10–13, 1995, Vienna, Austria, The Institute of Electrical and Electronics Engineers, Inc.

(List continued on next page.)

*Primary Examiner*—William E. Kamm
*Assistant Examiner*—George R. Evanisko
*Attorney, Agent, or Firm*—Woodard, Emhardt, Naughton, Moriarty & McNett

[57] ABSTRACT

A closed-loop, variable-frequency, vagal-stimulation apparatus for control of ventricular rate during atrial fibrillation. In one embodiment the apparatus includes a stimulator applied to the left vagus nerve and a controller programmed to automatically and continuously adjust the vagal stimulation frequency as a function of the difference between actual and desired ventricular excitation rates. In a second embodiment the apparatus includes a vagal nerve stimulator and a controller which automatically adjusts the vagal stimulation frequency as a function of the difference between ventricular excitation rate and arterial pulse rate in order to eliminate or minimize pulse deficit.

19 Claims, 7 Drawing Sheets

OTHER PUBLICATIONS

Tim K. Peters, H.E. Koralewski and E. Zerbst, "The Principle of Electrical Carotid Sinus Nerve Stimulation: A Nerve Pacemaker System for Angina Pectoris and Hypertension Therapy", *Annals of Biomedical Engineering*, vol. 8, pp. 445–458, 1980.

Terry B. Cooper, Gilbert R. Hageman, Thomas N. James, and Albert L. Waldo, "Neural Effects on Sinus Rate and Atrioventricular Conduction Produced by Electrical Stimulation from a Transvenous Electrode Catheter in the Canine Right Pulmonary Artery" *Circulation Research*, vol. 46, No. 1, Jan., 1980.

Aydin M. Bilgutay, M.D., Ilhan M. Bilgutay, B.E.E., Frederick K. Merkel, M.D., and C. Walton Lillehei, Ph.D., M.D., "Vagal Tuning", *Journal of Thoracic and Cardiovascular Surgery*. vol. 56, No. 1, Jul., 1968.

P.E. Konrad, Ph.D., W.A. Tacker, Jr., M.D., Ph.D., J.D. Bourland, Ph.D., L.A. Geddes, Ph.D., and D. Hood, R.V.T., R.N., "A New Implantable Arterial Pulse Sensor for Detectio of Ventricular Fibrillation", *Medical Instrumentation*, vol. 22, No. 6, Dec., 1988.

Alfred E. Cohn and Thomas Lewis, "The Predominant Influence of the Left Vagus Nerve Upon Conduction Between the Auricles and Ventricles in the Dog," *The Journal of Experimental Medicine*, vol. XVII, 1913.

Leslie A. Geddes, Neal E. Fearnot, and Heidi J. Smith, "The Exercise–Responsive Cardiac Pacemaker," *IEEE Transactions on Biomedical Engineering*, Vo. BME–31, No. 12, Dec. 1984.

Leslie A. Geddes, Table 8.1 from *Cardiovascular Devices by Geddes*, Wiley, 1984.

John F. Fulton, M.D., Chapter 34, pp. 683 and 686, from *A Textbook of Physiology*, W.B. Saunders Company, 1955.

Paul Martin, "Dynamic Vagal Control of Atrial–Ventricular Condition: Theoretical and Experimental Studies," *Annals of Biomedical Engineering*, 3, 275–295, Feb. 28, 1975.

METHOD AND APPARATUS USING VAGAL STIMULATION FOR CONTROL OF VENTRICULAR RATE DURING ATRIAL FIBRILLATION

CROSS-REFERENCED TO RELATED APPLICATION

This application is a continuation-in-part of application Ser. No. 08/624,109, filed Mar. 29, 1996, now U.S. Pat. No. 5,690,681, issued Nov. 25, 1997.

BACKGROUND OF THE INVENTION

This invention relates to devices and methods for controlling ventricular rate during atrial fibrillation, and more particularly to such devices and methods employing nerve stimulation techniques.

Atrial tachycardia, flutter and fibrillation are serious arrhythmias resulting in a low cardiac output and limited exercise tolerance. At present these arrhythmias are treated with drugs, electric shock (cardioversion), or surgical destruction of the atrioventricular (A-V) node and pacemaker implantation. Surgical cutting of atrial tissue to eliminate re-entrant paths is now being investigated. Drug therapy is not always effective and there are undesirable side effects. Although cardioversion abolishes some of these atrial arrhythmias, they usually return because the cause for the arrhythmia is still present. Surgical ablation of the A-V node is successful but leaves the subject with a limited exercise tolerance unless a rate-responsive pacemaker is implanted. These existing approaches are accepted by the medical community and biomedical engineers as the only practical choices, despite the existence of research reported in the literature for years on the subject of electrophysiological techniques involving stimulation of various nerves.

To understand the mechanism of action of an alternative system, proposed herein, for ventricular rate control by means of control of the number of atrial excitations reaching the ventricles, it is useful to review some aspects of the effect of cholinergic drive on the heart. Acetylcholine hyperpolarizes the S-A node and atrial muscle membranes, reduces the refractory period of atrial muscle and weakens the force of atrial contraction. Cholinergic drive also delays or blocks the transmission of excitation across the A-V node.

The cholinergic nerves to the heart are the right and left vagii. The right vagus innervates the S-A node, the atrial muscle and, to a much lesser degree, the A-V node. The left vagus nerve innervates the S-A node and atrial muscle to a lesser degree than it innervates the A-V node. It is well known to physiologists that stimulation of the right vagus nerve predominately slows the S-A node rate and thereby reduces heart rate. Stimulation of the left vagus nerve produces some slowing of the S-A node, prolongation of A-V conduction and partial or total A-V block. We have observed in monophasic atrial electrograms that low-frequency left vagal stimulation causes a dramatic shortening of the duration of the atrial monophasic action potential, indicating shortening of the atrial refractory period. Although the left vagus nerve affects atrial rate to a lesser degree, transmission of excitation across the A-V node is largely regulated by the left vagus nerve.

In atrial fibrillation, the A-V node is bombarded with excitations and responds as rapidly as its refractory period will allow, resulting in rapid, irregular ventricular excitations, i.e., R waves, resulting in varying times for ventricular filling. This results in a rapid, irregular pulse with a pulse deficit. A pulse deficit exists when a ventricular excitation (R wave) does not produce a blood pressure pulse. The mean blood pressure and cardiac output are both reduced as a result of the pulse deficit.

There have been some reports of using electrodes to stimulate the vagus nerve, where such stimulation has an effect on heart rhythm. See, e.g., Bilgutay et al., Vagal Tuning, *J. Thoracic Cardiovas. Surg.* 56(1):71–82, July, 1968. Bilgutay et al. studied the use of right vagal stimulation for treatment of supraventricular arrhythmias, angina pectoris, and heart failure. Experiments were conducted to determine the effective amplitudes, frequencies, wave shapes and pulse length of the stimulating current to achieve an optimal slowing of the heart rate by stimulating the vagus nerve, the optimal heart rate being defined as the slowest heart rate that could be attained by vagal stimulation without causing A-V dissociation or complete heart block or lowering the ventricular and aortic pressures. The experiments involved the right vagus nerve and resulted in selection of a stimulation amplitude of 6 to 10 volts, a frequency of 10 pulses per second, and 0.2 msec. pulse duration. Voltage increases were noted to decrease heart rate, and a unit triggered by the R waves of the subject's electrocardiogram is described as operating on a servo principle, but apparently in all cases the amplitude and frequency settings are fixed whenever the unit is operating. Bilgutay et al. indicated that the right vagus nerve was stimulated because its distribution is known to be mostly to the sinoatrial node area, but mentioned one experiment in which stimulation of the left vagus slowed the ventricular rate in a dog with complete heart block.

Recognizing the possibility of bradyarrhythmia, one recently proposed approach contemplates the inclusion of cardiac pacing with vagal stimulation. This latter approach to ventricular rate control, which entails a bradyarrhythmia pacemaker, is described in U.S. Pat. No. 5,330,507 to Schwartz. The addition of pacemaker circuitry and related components naturally increases the complexity and cost of the medical device. The patent mentions that stimulation frequency may be varied in a predetermined pattern from an optimum stimulation frequency, amplitude and duration determined during patient workup, if the initial delivered therapy fails to convert the tachyarrhythmia; however, there is no indication of a suitable pattern or any method of implementing it. The device described is designed to generate nerve stimulating pulses having a frequency and amplitude that, while programmable, are fixed once programmed. In essence it is an ON/OFF device that switches state in response to, e.g., the crossing of a heart rate threshold. Such ON/OFF switching, with fixed pulse characteristics, is likely to produce a hunting response, i.e., cycling of the heart rate with episodes of tachycardia. Moreover, although mentioning atrial fibrillation, this patent focuses on prevention or interruption of tachyarrhythmia, and contains no apparent recognition or appreciation that atrial fibrillation can be allowed to persist and that stimulation of the left vagus nerve, as opposed to the right vagus, is necessary and sufficient to effectively control the ventricular rate during atrial fibrillation.

U.S. Pat. No. 5,203,326 to Collins discloses a pacemaker which detects a cardiac abnormality and responds with pacing combined with vagal nerve stimulation. Collins discloses a method of vagal stimulation which includes progressively increasing the stimulation frequency in one-minute intervals and, for the pulse delivery rate selected, slowing the heart rate to a desired, stable level by increasing the pulse current. In the illustrated waveforms (FIGS. 12A–D), there is no correlation between stimulation frequency and ventricular rate. Moreover, the method is open-loop, without regard for the difference between the current rate and a desired rate.

There is also no teaching or suggestion that a simplified device without pacing capability could provide effective control of ventricular rate through vagal stimulation while allowing atrial fibrillation to persist. Furthermore, one of ordinary skill in the art would not read the Collins patent as teaching or suggesting that it is the left vagus nerve that must be stimulated to provide effective control of ventricular rate during atrial fibrillation.

Another device using vagal stimulation for treating tachyarrhythmia is disclosed in a European patent application published in 1995 as Publication No. EP0688577A1. This device is designed to terminate fibrillation by vagal stimulation. There is no disclosure of a method for controlling ventricular rate by vagal stimulation while atrial fibrillation is ongoing and no mention of the use of the left vagus nerve for that purpose.

Thus there remains the need for a system that effectively takes advantage of the phenomenon that transmission across the A-V node is largely, but not entirely, regulated by the left vagus nerve, and, more particularly, provides effective control of electrical stimulation of the vagus nerve to control the number of excitations that reach the ventricles during atrial fibrillation.

SUMMARY OF THE INVENTION

The present invention overcomes the foregoing and other disadvantages of the prior art by providing a closed-loop, variable frequency vagal stimulation apparatus for control of ventricular rate during atrial fibrillation. The apparatus includes a stimulating means for stimulating the left vagus nerve at a stimulation frequency which is varied automatically in response to sensed conditions, and a controller having an output connected to said stimulating means and including means for automatically and continuously adjusting said left vagal stimulation frequency as a function of the difference between actual and desired ventricular excitation rates.

According to another aspect of the present invention, there is provided an apparatus for automatically controlling ventricular rate by vagal stimulation to minimize pulse deficit during atrial fibrillation. The apparatus includes a stimulating means for stimulating the left vagus nerve at a stimulation frequency which is varied automatically in response to sensed conditions, a means for detecting a ventricular excitation rate, a means for detecting an arterial pulse rate, and a processing means for comparing said ventricular excitation rate and said arterial pulse rate and automatically adjusting said vagal stimulation frequency as a function of the difference between said ventricular excitation rate and said arterial pulse rate.

A general object of the present invention is to provide an improved method and apparatus for controlling ventricular rate in the presence of atrial fibrillation.

A further object is to provide effective control of ventricular rate via vagal stimulation.

Another object of the invention is to provide an effective method and apparatus for stimulating the left vagus nerve and thereby reducing ventricular rate enough to eliminate or minimize the pulse deficit which typically occurs during atrial fibrillation.

DETAILED DESCRIPTION OF THE PREFERRED EMBODIMENT

Figure 1:
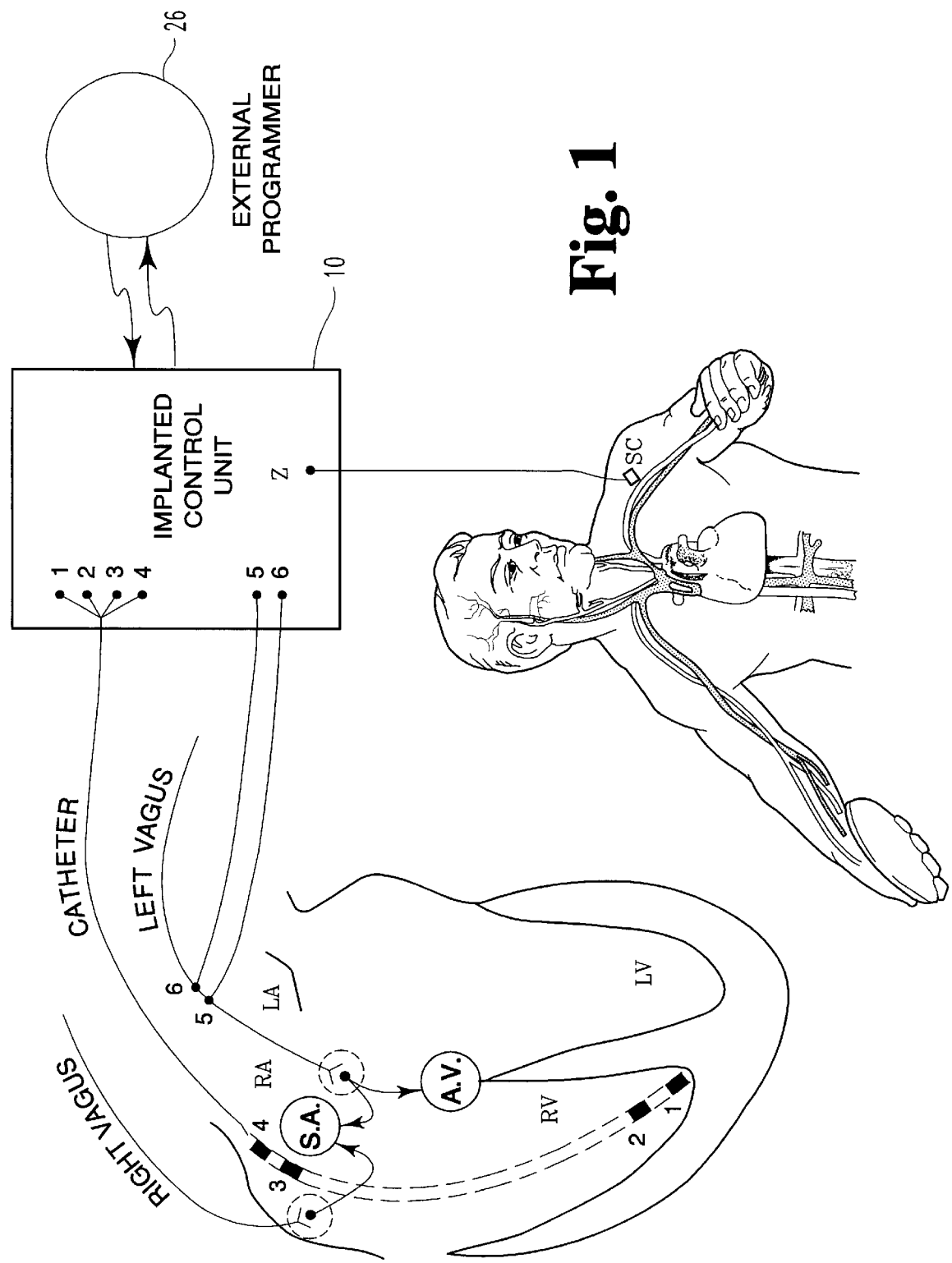
FIG. 1 is an illustration of an implanted control unit according to the present invention in its operating environment showing the heart and left and right vagus nerves.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 illustrates an implantable device according to the present invention in its operating environment in a mammalian body, in which it is operatively connected to the heart and the left vagus nerve. Information on the electrical activity of the ventricles and the atria is obtained by a catheter having two pairs of electrodes: electrodes 1 and 2 in the right ventricle (RV) and electrodes 3 and 4 in the right atrium (RA). Electrodes 1 and 2 are designed and positioned to detect a ventricular electrogram, which is supplied to the implanted controller unit 10 which processes the ventricular electrogram and derives therefrom the ventricular excitation rate. Electrodes 3 and 4 are designed and positioned to detect an atrial electrogram, which is supplied via the catheter to the implanted control unit, which processes the atrial electrogram. The implanted control unit includes logic circuitry or other circuit means for comparing the atrial and ventricular signals in terms of synchronization and rate, and on the basis of that comparison determining whether or not the patient is experiencing atrial fibrillation. The implantable device includes a pair of electrodes 5 and 6 attached or adjacent to the left vagus nerve for controlled stimulation thereof. One embodiment of the present invention, described below, also includes a sensor of the arterial blood pressure pulse, in the form of a monopolar impedance-measuring electrode applied to the surface of the subclavian (SC) or other convenient artery. Alternately, a piezoelectric pulse pickup placed alongside an artery could be used. A piezoelectric device would generate a voltage pulse and therefore save battery life in an implanted control unit dependent on a battery for operation.

The two embodiments of the invention to be described below are desirably combined in a single implanted control unit operable in two modes respectively associated with the control algorithms for the first and second embodiments. Both embodiments use an adaptive control system which adjusts to changing cardiac states. It operates only during episodes of atrial fibrillation. It retains, in memory, parameters that were successful in previous episodes of required control and uses this previously learned information to improve controller responses under similar situations. It also uses this information to update controller adjustments in newly encountered situations.

The first embodiment and its associated algorithm will be described in connection with FIG. 2, which depicts in block diagram form a controller 20 as an important aspect of the implanted control unit. The ventricular and atrial signals are supplied from their respective electrodes in the heart to a ventricular electrogram detector 22 and atrial electrogram detector 24, respectively, which digitize the electrograms and supply the digitized signals to controller 20, which responds to the detected ventricular and atrial signals.

Figure 6:
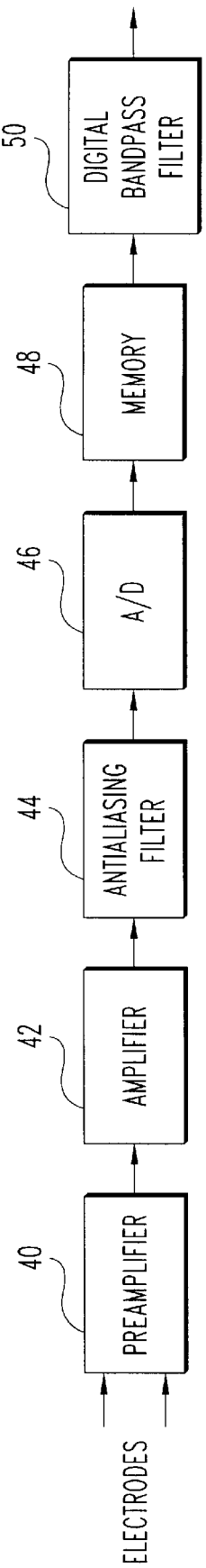
FIG. 6 is a block diagram of the electrogram detectors in FIGS. 2 and 3 and of the arterial pulse detector of FIG. 3.

Electrogram detectors 22 and 24 are shown in further detail in FIG. 6, from which it will be appreciated by those skilled in the art that the electrical activity from the associated electrodes is preamplified (in block 40), amplified (in block 42), and passed through an antialiasing filter 44 prior to sampling in an A/D converter 46. The sampled electrogram is then stored in a data buffer 48. The data are recalled from memory and bandpass filtered in filter 50 with a passband selected to maximize the signal-to-noise ratio. For example, in the case of the ventricular electrogram detector, the passband is selected to maximize the ratio of QRS complexes to T-waves and other noise sources. The bandpass filtered signal is then sent to a signal preprocessor in the controller, as will be described.

Atrial rate can be determined on the basis of the interval between atrial waves and is compared to a threshold established as an indication of atrial fibrillation. If desired, the time interval itself may be measured and compared to a time interval threshold for the same purpose.

Figure 7A:
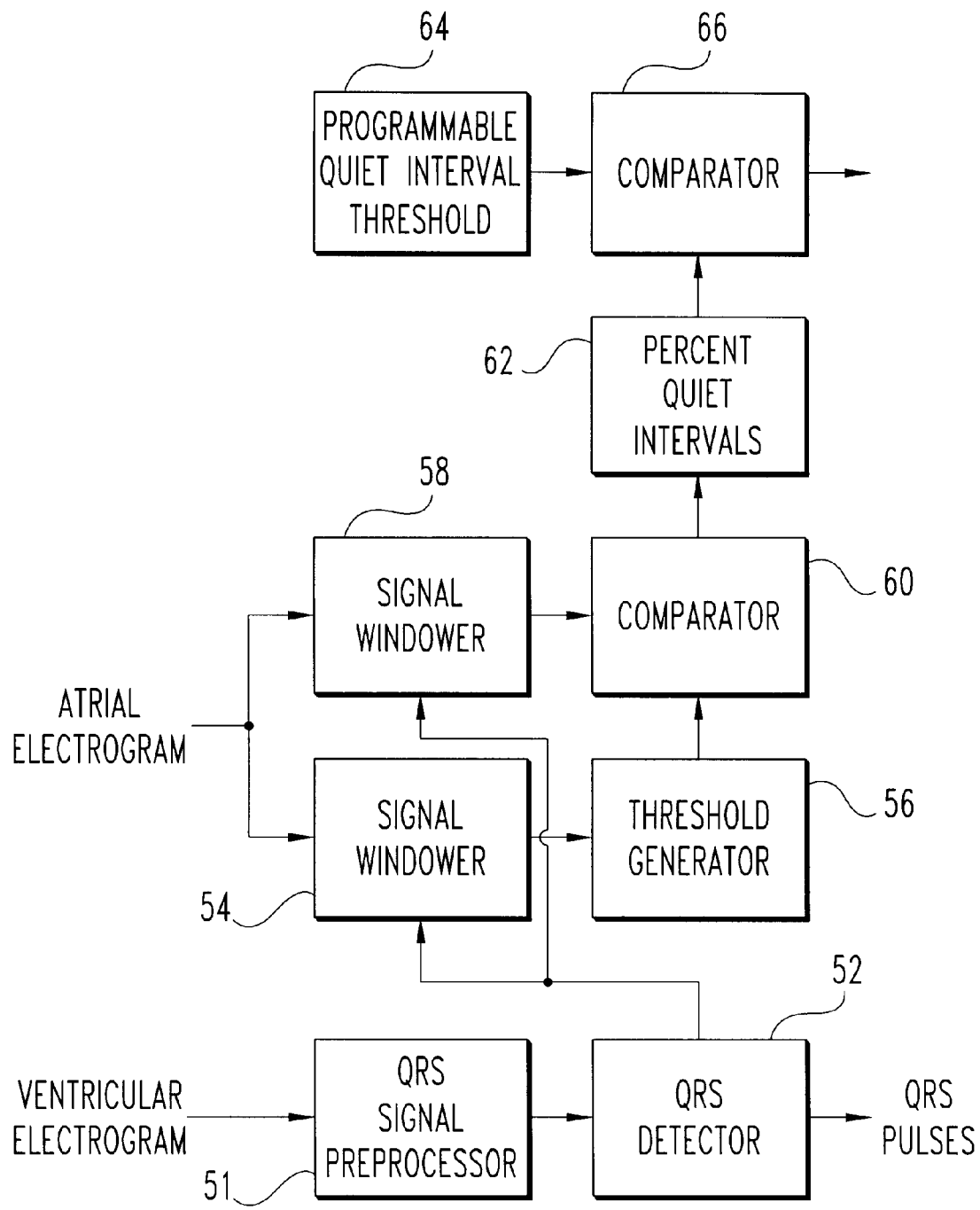
FIG. 7A is a block diagram of the atrial fibrillation detector incorporated in each controller of FIGS. 2 and 3 and preferably in a common controller.

Preferably, sufficient hardware and software are combined in a common controller to detect atrial fibrillation, and also to selectively implement a targeted rate algorithm or a pulse deficit algorithm, or a weighted combination of those algorithms, as will be described. Such a common controller is depicted in block diagram form in FIGS. 7A–C. In the presently preferred form of atrial fibrillation detector, shown in block diagram form in FIG. 7A, the atrial electrogram is examined in the time windows between QRS complexes, that is, between the rectangular pulses in a derived ventricular timing signal. Detection of QRS complexes is performed with a QRS signal preprocessor 51 and an adaptive threshold detector 52. The preprocessor takes the derivative of the ventricular electrogram signal from the output of detector 22, squares it, and then integrates it. This preprocessed signal is sent to detector 52 and to a peak detector therein which both detects peaks and classifies peaks as either signal (QRS complexes) or noise (T-waves or other noise sources). Using this information, obtained during a moving window of programmable width, e.g., four seconds, an adaptive threshold is computed which is above the noise and T-wave peak values. This adaptive threshold for the most recent moving window is compared to the incoming preprocessed signal, and, when the preprocessed signal exceeds the adaptive threshold, a QRS complex is determined to be found. The QRS pulses as detected by detector 52 are supplied to signal windowers 54 and 58 and also, as will be described with reference to FIG. 7B, to a counter 70 for determination of ventricular rate.

In atrial fibrillation, the atria are not electrically silent in the time windows between QRS complexes. An atrial electrical activity threshold is derived in threshold generator 56 by computing a percentage of the average value of all peaks found in the atrial electrogram as supplied by signal windower 54 during these time windows. More specifically, it has been found suitable to initiate a four-second interval and then average the largest atrial values detected during the time windows between QRS complexes which occur in the four-second interval, and to set the threshold as one-third the average value. This threshold is used in comparator 60 to reexamine the atrial electrogram during a fixed-width window of programmable width, defined by windower 58, following the end of a detected QRS complex. A width of 150 msec. has been found suitable. If the atrial electrogram amplitude is below the computed threshold for a specific window, that window is determined to be a "quiet interval." The number of quiet intervals is determined in a preselected period of time, e.g., four seconds. The percentage of quiet intervals is determined in block 62 by dividing the number of quiet intervals by the total number of intervals. If the percentage of quiet intervals is less than a preprogrammed threshold value (in block 64), e.g., forty percent (40%), atrial fibrillation is determined by comparator 66 to be present, whereupon the controller is enabled to implement the selected ventricular rate control algorithm.

Other techniques and algorithms for detection of atrial fibrillation with a lead configuration of multiple catheters including one in the right atrium and another in the coronary sinus are disclosed in an article by Kim et al. entitled "An Atrial Fibrillation Detection Algorithm for an Implantable Atrial Defibrillator", *Computers in Cardiology*, 1995, IEEE 1995: 169–172, which article is hereby incorporated by reference.

In the presence of atrial fibrillation, the controller is enabled to compare the actual R-wave rate with a target rate 25 entered into the controller via an external programmer 26 (FIG. 1) and, based on the difference between those rates, to control the frequency of the pulses which it generates and supplies to a stimulator 28 connected via electrodes 5 and 6 to the left vagus nerve. The controller includes an internal transmitter/receiver (not shown) adapted to establish a two-way telemetry link with external programmer 26, whereby telemetry information may be supplied to and from the controller's internal memory. The controller may be programmed to apply a low initial frequency, and consequently, to increase the stimulus frequency slowly and incrementally until the ventricular rate matches the operator-selected target rate. Preferably, the controller is programmed to automatically and continuously adjust the vagal stimulation frequency, e.g., at one-second intervals, as a function of the difference between the actual and desired ventricular excitation rates.

Figure 7B:
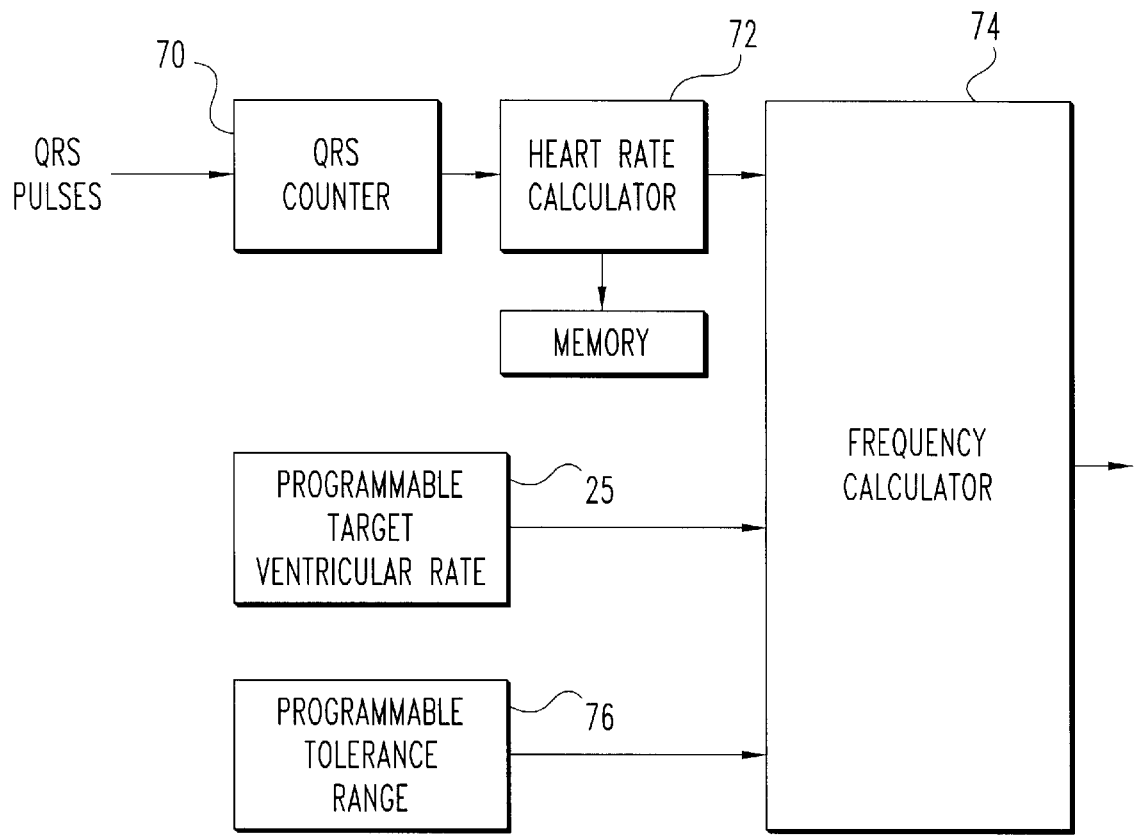
FIG. 7B is a block diagram of the targeted ventricular rate algorithm portion of the controller.
Figure 7C:
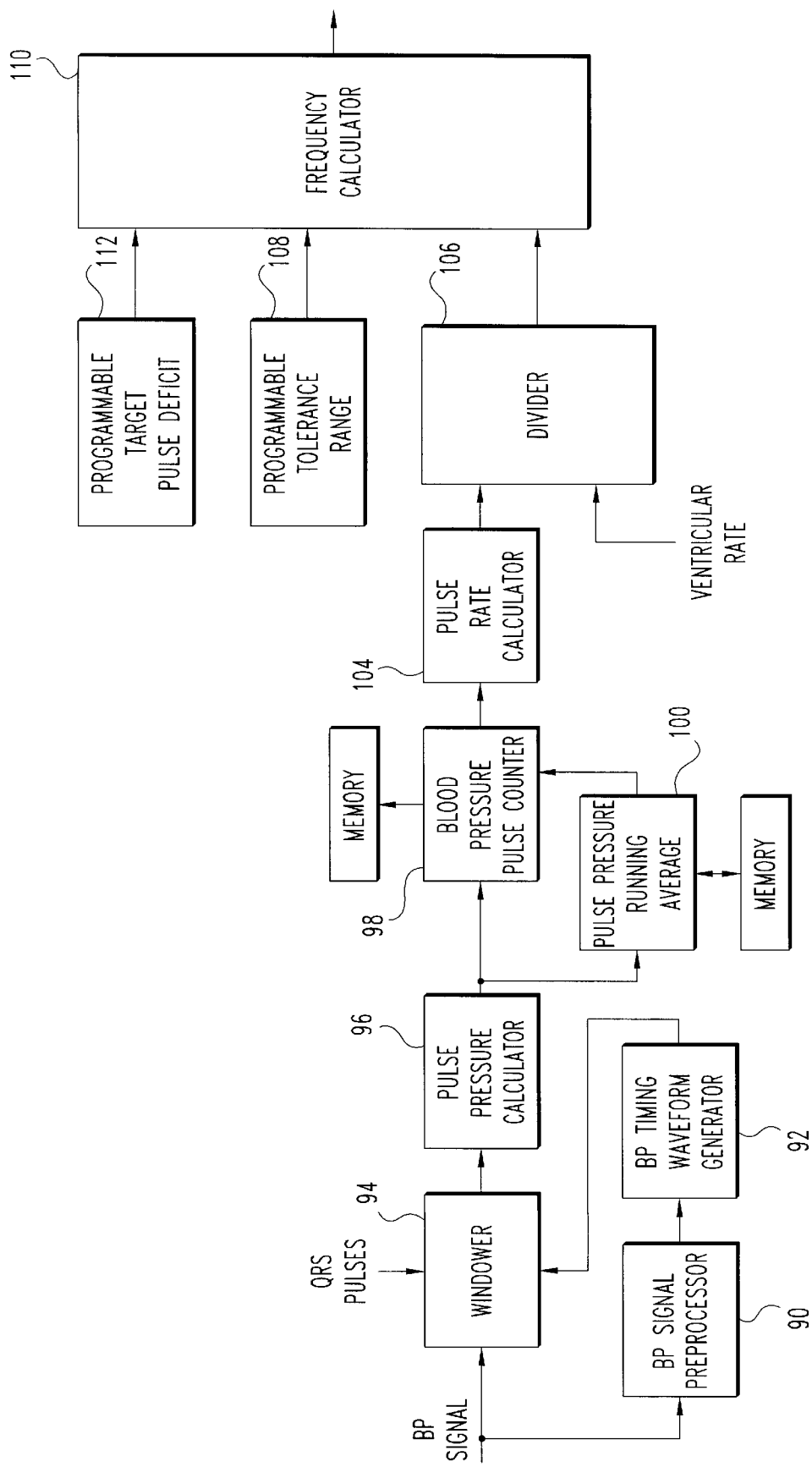
FIG. 7C is a block diagram of the pulse deficit algorithm portion of the controller.

More specifically, and with reference to FIG. 7B, the actual ventricular rate is determined by first counting (in block 70) the QRS complexes detected with adaptive threshold detector 52 (FIG. 7A) and then, in block 72, dividing the QRS count by the time interval over which the count was obtained, e.g., four seconds. If the actual ventricular rate exceeds the target rate (block 25) by more than a preprogrammed acceptable error, or in other words is outside a tolerance range as denoted in block 76, frequency calculator 74 establishes a vagal stimulation frequency and generates an appropriate output pulse which, when processed by stimulator 28, becomes a stimulation pulse for the left vagus nerve. The vagal stimulation frequency for ventricular rate control, $SF_{VR}$, is determined in the following manner. First a normalized deviation (ND(x)) from the programmed targeted ventricular rate is computed by subtracting the target rate from the actual value of the ventricular rate and dividing the result by the programmed tolerance range. The controller then takes a percentage of this deviation (by multiplying by $K_1$) and adds this value to the previous value of vagal stimulation frequency. In terms of an equation, $$SF_{VR}(x)=SF_{VR}(x-1)+K_1*ND(x)$$

where x is the epoch number.

If the actual ventricular rate is greater than the targeted ventricular rate, ND(x) will be positive, and vagal stimulation frequency will be increased. If the actual average ventricular rate is less than the targeted ventricular rate, ND(x) will be negative, and vagal stimulation frequency will be decreased. This is the physiologically appropriate action. The controller may be programmed to provide some nominal low initial stimulation frequency, e.g., 1–2 pulses/second, or may start with no stimulation, i.e., zero pulses/second.

The stimulation frequency and the coefficient $K_1$ are measured in pulses/second (or Hz), and a suitable value of $K_1$ is 0.1. A typical target rate is 80 bpm, and a nominal tolerance range is 10 bpm (a tolerance of ±5 bpm), although either one or both may be set higher or lower depending upon patient age and condition. The value of $K_1$ is preferably set to provide a change in stimulation frequency of approximately 0.5 pulses/second per update at the beginning of vagal stimulation. For example, with a target rate of 80 bpm, a tolerance range of 10 bpm, and $K_1$ equal to 0.1 pulses/second, a patient with a ventricular rate of 130 bpm when atrial fibrillation is detected would experience an initial change in stimulation frequency of 0.5 pulses/second:

$$\Delta SF_{VR}=(0.1)*(130-80/10)=0.5 \text{ pulses/second}$$

Vagal stimulation frequency will increase or decrease in larger or smaller steps depending upon the magnitude of the difference between actual ventricular rate and the targeted ventricular rate. Thus a large deviation in ventricular rate is counteracted quickly by increasing the vagal stimulation frequency by a proportionately large amount. Small rate deviations are adjusted by small vagal stimulation frequency changes. When the actual ventricular rate equals the targeted ventricular rate or is otherwise within the tolerance range, the vagal stimulation frequency will be unchanged. Dividing by the tolerance range, which is twice the physician-entered tolerance, has the effect of bringing ventricular rate back into tolerance more quickly for cases when there is a small allowable tolerance in ventricular rate and more slowly for cases when a large tolerance is allowed. When the rate is back in tolerance, the most current stimulation frequency is stored for future use as the initial stimulation frequency in the event that the rate is out of the tolerance range again during atrial fibrillation. Alternatively, the frequency calculator, once enabled, may continue to adjust the stimulation frequency according to the above equation even after the ventricular rate is brought within tolerance, and until the atrial fibrillation ceases.

Figure 4:
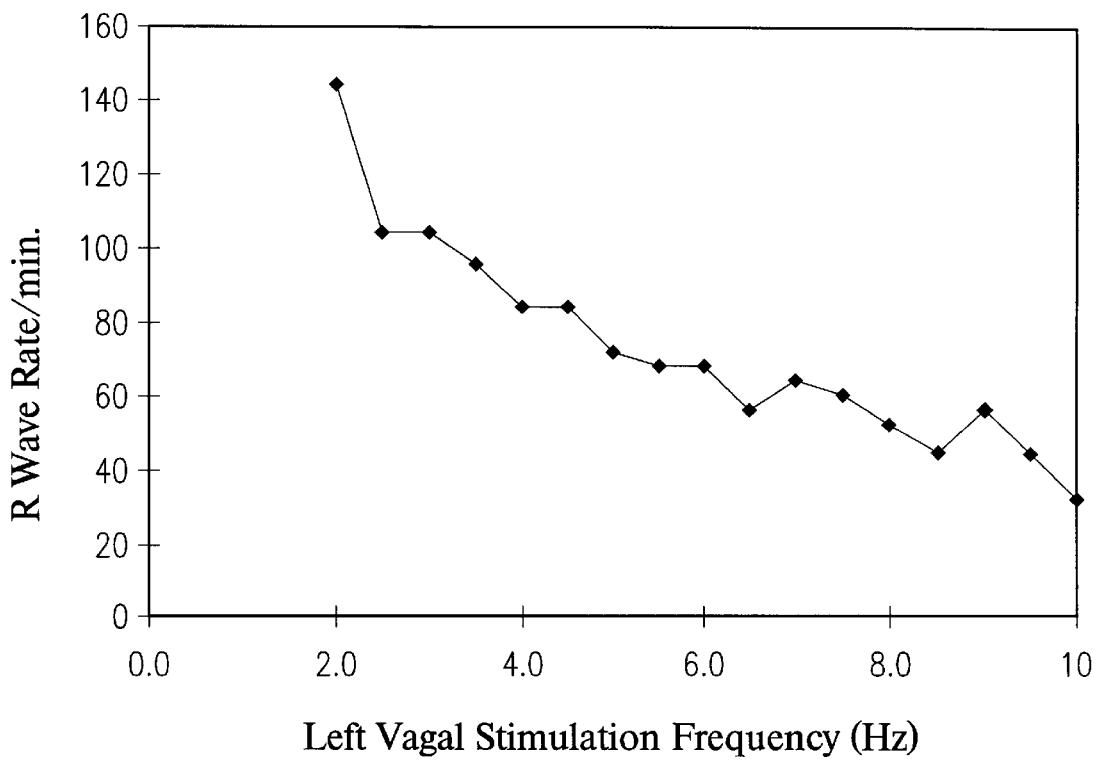
FIG. 4 is a graphical illustration of the relationship between ventricular rate and left vagal stimulation frequency during atrial fibrillation.

FIG. 4 illustrates the relationship between ventricular rate and left vagal stimulation frequency during atrial fibrillation. An increase in stimulation frequency caused the ventricular rate to be decreased smoothly, in an almost linear manner, down to a rate of 35 bpm with a stimulation frequency of 10 pulses/second. A stimulating pulse width of 100 microseconds ($\mu$sec.) has been found suitable, and pulse widths up to 2 msec. may also be effective in some applications. A pulse amplitude in the range of 1 to 25 volts supplied by stimulator 28 has been found suitable in the anesthetized dog.

Although less desirable than the time-based adjustment of stimulation frequency described above, adjustment based on ventricular rate relative to multiple thresholds may be suitable for some patients, with a predetermined threshold for each of several discrete levels of deviation from the desired rate. In this alternative embodiment, the controller has a programmable table of stimulation frequency differentials corresponding to the respective deviation thresholds, and the desired rate and a corresponding nominal vagal stimulation frequency are set by a physician during a patient workup. The frequency differentials, measured with respect to the nominal frequency, are preferably directly proportional to their respective rate deviation thresholds, but, alternatively, may be more or less than proportionately higher for higher rate thresholds.

It is anticipated that a fixed target ventricular rate will be sufficient to allow patients to conduct normal activities. A higher ventricular rate would be desirable for patients desiring to exercise, and it is contemplated that such a capability may be provided by incorporating an exercise sensor coupled to the controller so as to increase the targeted ventricular rate in response to exercise and thereby provide an automatic exercise capability for such patients. The exercise sensor may suitably respond to right ventricular blood temperature, respiratory rate, body motion, or other parameters, a number of which are described in a paper by Geddes et al. entitled: "The Exercise-Responsive Cardiac Pacemaker," *IEEE Transactions on Biomedical Engineering*, Vol. BME-31, No. 12, December 1984, which paper is hereby incorporated by reference. Another form of exercise sensor that may be utilized, employing an accelerometer technique, is described in U.S. Pat. No. 4,428,378, which is hereby incorporated by reference.

Figure 3:
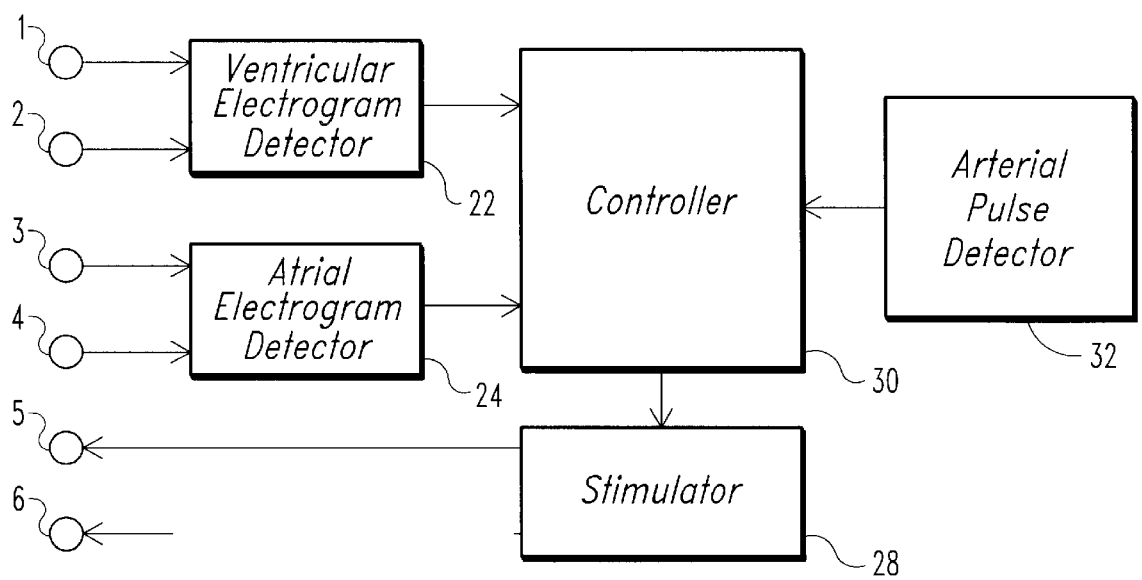
FIG. 3 is a block diagram of another form of the implanted control unit of FIG. 1.
Figure 5:
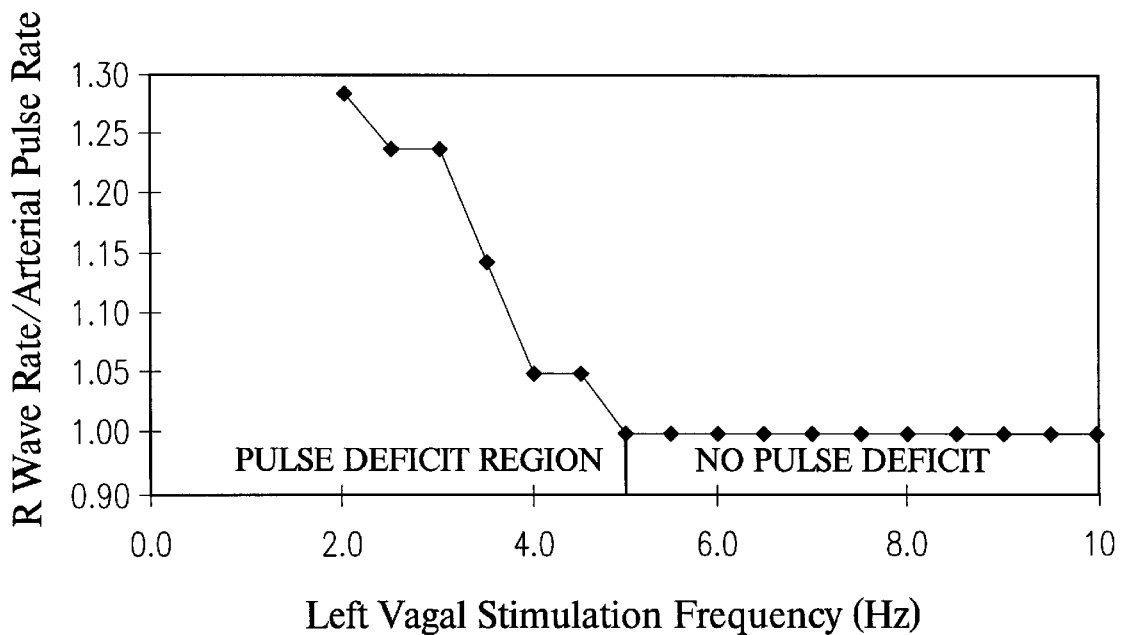
FIG. 5 is a graphical illustration of the ratio of R wave rate to arterial pulse rate versus the frequency of left vagal stimulation during atrial fibrillation.

Referring to FIG. 3, the second embodiment or mode of the present invention operates according to an algorithm designed for elimination of a pulse deficit, i.e., the condition in which an arterial pulse fails to occur in response to an R wave. This algorithm does not require the selection of a target ventricular rate and may therefore be operator-independent. The objective of this closed-loop control method is to identify the lowest stimulus frequency required to be applied to the left vagus nerve to achieve a ventricular rate with no pulse deficit. As will be described, the controller 30 is designed and programmed to monitor the blood pressure signal for an arterial pulse after every ventricular excitation (as indicated by the R wave of the ECG), and, in general terms, to use the pulse deficit to control the frequency of stimuli applied to the left vagus nerve in order to identify the minimum stimulus frequency for which each ventricular excitation produces a blood pressure pulse. The controller may be programmed to implement an algorithm corresponding generally to the graph illustrated in FIG. 5, although it will be understood that the shape and values of such a graph will vary somewhat for individual patients and that the automatic control algorithm will be varied accordingly. The ventricular and atrial electrogram detectors 22 and 24 digitize the electrogram signals and supply them to the controller, which also receives digitized data from an arterial pulse detector 32, which includes circuitry of the type shown in FIG. 6 and which is described in further detail below.

One consideration in achieving closed-loop control to eliminate the pulse deficit in atrial fibrillation is adoption of an amplitude criterion for arterial pulse counting. During atrial fibrillation, the arterial pulses vary widely in amplitude. However, a pulse should occur in a time window just after the R wave of the ECG, and so the R wave is preferably used to open a time window to measure the peak-to-peak amplitude of the arterial pulse in the window, which is sufficiently long to accommodate the isovolumic period of the ventricles and the pulse transit time to the arterial measuring site. In a typical situation the former is on the order of 150 msec. and with a measuring site close to the left ventricle, the latter may amount to 50–100 msec. A running average of the pulse amplitude is made, and each newly measured pulse is compared in amplitude to the mean pulse amplitude. Pulses less than a predetermined percentage (20% is presently preferred) of the mean pulse amplitude are treated as absent.

A pulse measurement window is also preferably derived from the blood pressure signal itself. Arterial pulse detector 32 supplies a bandpass filtered blood pressure pulse (BP) signal to a blood pressure pulse signal preprocessor 90 shown in the portion of the controller illustrated in FIG. 7C. The preprocessor differentiates the signal and truncates all negative components. The resultant signal is then used by waveform generator 92 to derive a blood pressure pulse timing signal containing rectangular pulses which are coincident in time with the ejection of blood into the arterial system from the heart and which have a pulse width equal to the duration of the blood ejection. That timing signal is supplied to windower 94 to establish the measurement window. Pulse pressure is calculated (block 96) by subtracting the minimum value of pulse pressure from the maximum value of pulse pressure during the measurement window. The measurement during a particular measurement window is considered valid only if that measurement window occurs within the time window after a detected QRS complex. Pulse counter 98 includes software or circuitry for determining the presence or absence of a blood pressure pulse by comparing the pulse amplitude from calculator 96 with a threshold value, such as a percentage of the running average of pulse amplitudes (block 100) as described above. The blood pressure pulse count is determined in counter 98 by summing all blood pressure pulses counted as being present. Arterial pulse rate is then determined in calculator 104 by dividing the blood pressure pulse count by the time interval over which the count was obtained, e.g., one minute. The pulse deficit is then calculated in terms of a ratio by dividing ventricular rate by arterial pulse rate in divider 106.

The amount of pulse deficit is identified by the relationship between R waves of the ECG and arterial pulse waves over a predetermined interval of time, for example, one minute. This interval may be a moving window providing for calculation of current pulse deficit once a second, but the one-minute calculation interval is preferred.

The vagal stimulation frequency for pulse deficit reduction, $SF_{PD}$, is then determined by the following equation:

$$SF_{PD}(x) = SF_{PD}(x-1) + K_2 * [PD(x) - PD_T] - K_3 * Y$$

First the difference between actual pulse deficit, $PD(x)$, and targeted pulse deficit, $PD_T$, is determined. Then a percentage of this difference (by multiplying by $K_2$) is added to the previous value of vagal stimulation frequency, $SF_{PD}(x-1)$. In addition, the vagal stimulation frequency can be decreased by the value of the term $K_3 * Y$, where Y is an integer and represents the number of epochs of the previous Z epochs for which there was no pulse deficit. The value of $K_3$ is programmable and in the preferred embodiment is less than $K_2$. A value of 0.25 pulses/sec/(R waves/arterial pulse) is suitable for $K_2$, where pulse deficit is measured in units of R waves per arterial pulse. A suitable value of $K_3$ is 0.0625 pulses/sec/epoch. Also in the preferred embodiment, the value for Z is 8.

The controller preferably has a programmable tolerance range, or error signal magnitude (block 108). That is, generation of stimulation pulses by the controller and incremental increase thereof occurs if the difference determined in comparator 110 between the target pulse deficit set in block 112 (preferably 1.0) and the actual pulse deficit is greater than a preprogrammed acceptable error, which may be ±0.05, or a tolerance range of 0.1. As with the ventricular rate control algorithm, the current stimulation frequency is maintained once the difference is within the tolerance range and is stored for future use as the initial stimulation frequency the next time the sensed conditions warrant vagal stimulation. The controller has a low R-wave rate safety limit, at which point the controller maintains the current stimulation frequency, in order to protect the patient from an excessively low ventricular rate; the safety limit is preferably programmable.

An arterial pulse detector 32 suitable for use with the present invention includes a monopolar arterial electrode made from a Teflon-coated stainless steel or other suitable wire, insulated except at its distal end, which is sutured to a small sheet of Dacron-reinforced Silastic. The Dacron sheet carrying the electrode is wrapped around the subclavian artery as shown in FIG. 1, or other convenient artery, and sutured. The monopolar arterial electrode operates in conjunction with a reference electrode which is relatively large and located at any convenient site, for example, the metal case of the implanted control unit. Further details of an arterial pulse detector as described above are described in an article by Konrad et al. entitled "A New Implantable Arterial Pulse Sensor for Detection of Ventricular Fibrillation," Medical Instrumentation 22(6):304–311, December, 1988, which article is hereby incorporated by reference. Alternatively, a cuff electrode could be used. For experimental studies, the arterial pulse may be measured directly, e.g., with a piezoelectric pulse pickup as indicated above.

A suitable electrode presently preferred for attachment to the left vagus nerve is a helical cuff electrode described in detail in U.S. Pat. No. 4,573,481, which is hereby incorporated by reference. Alternatively, for greater ease in mounting the electrode on the patient's nerve during implantation, the electrode may be in the shape of a bird's claw as disclosed in U.S. Pat. No. 5,215,089, which is hereby incorporated by reference.

If desired, stimulator 28 may be configured to receive pulses generated by the controller and to supply pulses to the left vagus nerve with a predetermined intensity and duration which are preferably variable and programmable. Alternatively, the stimulator may be configured essentially as an electrode driver circuit without separate pulse generation capability, i.e., limited to supplying voltage or current at a desired level, or it may be a separate programmable pulse generator having a rate control input coupled to a controller correspondingly designed to determine a stimulation frequency and to supply a corresponding command or signal to the rate control input of the pulse generator. The controller and stimulator may be implemented with a conventional microprocessor and associated output circuitry of the type disclosed in U.S. Pat. No. 5,154,172, which is hereby incorporated by reference.

Preferably, the two algorithms described above are implemented in combination to determine the appropriate vagal stimulation frequency. In particular, the stimulation frequency, SF(x), is determined by a weighted sum of the frequencies calculated by frequent calculations 74 and 110, according to the following equation:

$$SF(x) = W \cdot SF_{PD}(x) + (1-W) \cdot SF_{VR}(x)$$

where W is a weighting factor.

The permissible range of the weighting factor, W, is 0 to 1, and the preferred range is 0 to 0.6. The weighting factor and acceptable programmable tolerance ranges can be programmed according to patient needs. A new stimulation frequency is preferably calculated every second or at the same update rate as $S_{VR}$; consequently, the value of $SF_{PD}$ remains the same for 60 update cycles (one minute) in this weighted sum embodiment because $SF_{PD}$ is preferably only updated at one-minute intervals.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, those skilled in the art will appreciate from the foregoing teachings of the present invention that other embodiments can be used to implement the principle of ventricular rate control during atrial fibrillation using controlled left vagal stimulation. For example, both vagus nerves may be stimulated to obtain more A-V block. Alternately, only the cardiac branch of the left vagus nerves (left and/or right) may be stimulated to minimize any possible gastrointestinal effects. The left cervical vagus nerve is believed to advantageously require a low stimulus frequency, but its use has the potential side effect of increased gastrointestinal motility and secretion.

Figure 2:
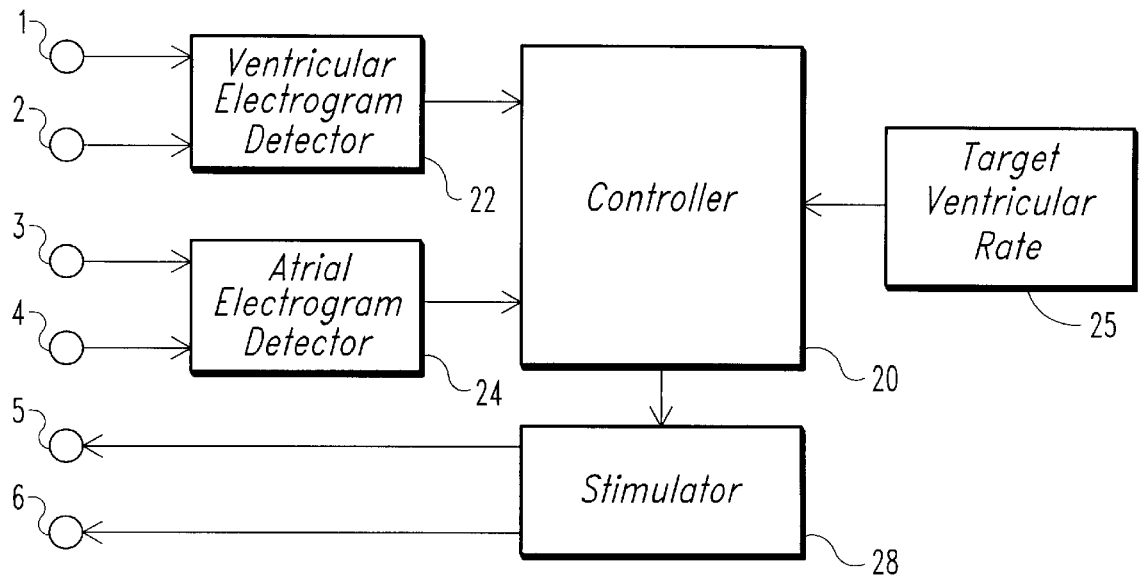
FIG. 2 is a block diagram of one form of the implanted control unit of FIG. 1.

The embodiments illustrated in FIGS. 1 and 2 employ a catheter electrode in the right atrium and ventricle and another electrode on the left vagus nerve. An alternate embodiment could use a catheter electrode in the right pulmonary artery to stimulate the left vagus nerve, as described by Cooper et al. (Circ. Res. 1980, 46:48–57). In this way, the principle can be applied using catheter electrodes.

Another embodiment avoids blood contact by using electrodes applied to the pericardium to detect the atrial and ventricular electrograms. Also, although less sensitive to those electrograms and more sensitive to noise, local subcutaneous sensing electrodes may be useful in certain situations, and they offer the advantage of enabling electrogram sensing without an A-V sensing lead in the heart.

We claim:

1. A closed-loop, variable-frequency, vagal-stimulation apparatus for control of ventricular rate during an ongoing atrial arrhythmia, comprising:

means for detecting an atrial arrhythmia;

means for sensing ventricular excitation rate;

means responsive to detection of said atrial arrhythmia for generating pulses for stimulation of the left vagus nerve at a stimulation frequency which is variable automatically as a function of the difference between actual and desired ventricular excitation rates, said adjusting means including means for changing said vagal stimulation frequency by a greater amount for one value of said ventricular rate difference than for a smaller value of said ventricular rate difference; and means for delivering said pulses to said left vagus nerve.

2. The apparatus of claim 1, further comprising means for enabling generation of stimulating pulses by said generating means only in the presence of atrial fibrillation.

3. The apparatus of claim 2, wherein said means for sensing ventricular excitation rate senses QRS complexes and determines ventricular excitation rate therefrom.

4. The apparatus of claim 3, wherein said adjusting means includes means for changing said vagal stimulation frequency over a predetermined time interval by a greater amount for said one value than for said smaller value.

5. The apparatus of claim 4, wherein said adjusting means includes means for calculating a normalized deviation from said desired ventricular rate based on a predetermined tolerance value.

6. The apparatus of claim 5, wherein said adjusting means includes means for adding a value directly proportional to said normalized deviation to the vagal stimulation frequency to obtain a new vagal stimulation frequency.

7. The apparatus of claim 6, wherein said adjusting means includes means for adjusting said vagal stimulation frequency at intervals of approximately one second.

8. The apparatus of claim 1, wherein said adjusting means includes means for calculating a normalized deviation from said desired ventricular rate based on a predetermined tolerance value.

9. The apparatus of claim 1, wherein said adjusting means includes means for adding a value directly proportional to said ventricular rate difference to the vagal stimulation frequency to obtain a new vagal stimulation frequency.

10. A closed-loop, variable-frequency, vagal-stimulation method for control of ventricular rate during an ongoing atrial arrhythmia, comprising:

detecting an atrial arrhythmia;

sensing ventricular excitation rate;

automatically, upon detection of said atrial arrhythmia, determining a left vagal stimulation frequency and automatically adjusting said vagal stimulation frequency as a function of the difference between actual and desired ventricular excitation rates, said adjusting step including changing said vagal stimulation frequency by a greater amount for one value of said ventricular rate difference than for a smaller value of said ventricular rate difference;

generating pulses at said vagal stimulation frequency; and delivering said pulses to a left vagus nerve.

11. The method of claim 10, further comprising the step of enabling generation of stimulating pulses only in the presence of atrial fibrillation.

12. The method of claim 11, wherein said sensing step includes sensing QRS complexes.

13. The method of claim 12, wherein said adjusting step includes changing said vagal stimulation frequency over a given time interval by a greater amount for said one value than for said smaller value.

14. The method of claim 13, wherein said adjusting step includes calculating a normalized deviation from said desired ventricular rate based on a predetermined tolerance value.

15. The method of claim 14, wherein said adjusting step includes adding a value directly proportional to said normalized deviation to the vagal stimulation frequency to obtain a new vagal stimulation frequency.

16. The method of claim 15, wherein said adjusting step includes adjusting said vagal stimulation frequency at intervals of approximately one second.

17. The method of claim 10, wherein said adjusting step includes calculating a normalized deviation from said desired ventricular rate based on a predetermined tolerance value.

18. The method of claim 10, wherein said adjusting step includes adding a value directly proportional to said ventricular rate difference to the vagal stimulation frequency to obtain a new vagal stimulation frequency.

19. A closed-loop, variable-frequency, vagal-stimulation method of controlling ventricular rate during atrial fibrillation without electrical stimulation of the heart, comprising:

detecting atrial fibrillation;

allowing said atrial fibrillation to persist;

sensing ventricular rate;

automatically, upon detection of said atrial fibrillation, determining a left vagal stimulation frequency in response to sensed ventricular rate relative to a desired value of ventricular rate, said determining step including increasing said vagal stimulation frequency by an amount directly proportional to a detected difference between sensed and desired ventricular excitation rates;

stimulating a left vagus nerve at said vagal stimulation frequency during said atrial fibrillation; and terminating said vagal stimulation frequency upon cessation of said atrial fibrillation.

\* \* \* \* \*